(12) United States Patent
Teague et al.

(10) Patent No.: US 10,605,069 B2
(45) Date of Patent: Mar. 31, 2020

(54) METHODS AND MEANS FOR CASING, PERFORATION AND SAND-SCREEN EVALUATION USING BACKSCATTERED X-RAY RADIATION IN A WELLBORE ENVIRONMENT

(71) Applicants: Philip Teague, Houston, TX (US); Melissa Spannuth, Houston, TX (US)

(72) Inventors: Philip Teague, Houston, TX (US); Melissa Spannuth, Houston, TX (US)

(73) Assignee: Visuray Intech Ltd (BVI), Road Town, Tortola (VG)

( * ) Notice: Subject to any disclaimer, the term of this patent is extended or adjusted under 35 U.S.C. 154(b) by 0 days.

(21) Appl. No.: 16/386,023

(22) Filed: Apr. 16, 2019

(65) Prior Publication Data
US 2019/0242239 A1    Aug. 8, 2019

Related U.S. Application Data

(62) Division of application No. 16/162,971, filed on Oct. 17, 2018.
(Continued)

(51) Int. Cl.
*E21B 47/00* (2012.01)
*H01J 35/02* (2006.01)
(Continued)

(52) U.S. Cl.
CPC ....... *E21B 47/0002* (2013.01); *G01N 23/203* (2013.01); *G01V 5/12* (2013.01);
(Continued)

(58) Field of Classification Search
CPC .... E21B 47/0002; G01N 23/203; G01V 5/12; H01J 35/02; H01J 35/025; H01J 35/32
See application file for complete search history.

(56) References Cited

U.S. PATENT DOCUMENTS

| 2009/0276158 A1* | 11/2009 | Kirkwood | G01V 5/101 702/8 |
| 2015/0177409 A1* | 6/2015 | Sofiienko | G01V 5/125 250/269.1 |

OTHER PUBLICATIONS

Teague, Philip Neil, Imaging of Backscattered Ionizing Radiation—A Key Enabler for through Mud Borehole Imaging:, OTC 21667, Presentation in Houston, Texas on May 2-5, 2011, (16 pages). (Year: 2011).*

* cited by examiner

*Primary Examiner* — Mark R Gaworecki
(74) *Attorney, Agent, or Firm* — Raymond R. Ferrera; Adams and Rees LLP

(57) ABSTRACT

An x-ray-based cased wellbore environment imaging tool is provided, the tool including at least an x-ray source; a radiation shield to define the output form of the produced x-rays; a direction controllable two-dimensional per-pixel collimated imaging detector array; sonde-dependent electronics; and a plurality of tool logic electronics and PSUs. A method of using an x-ray-based cased wellbore environment imaging tool to monitor and determine the integrity of materials within wellbore environments is also provided, the method including at least: producing x-rays in a shaped output; measuring the intensity of backscatter x-rays returning from materials surrounding the wellbore; controlling two-dimensional per-pixel collimated imaging detector arrays; and converting image data from said detectors into consolidated images of the wellbore materials.

10 Claims, 2 Drawing Sheets

Related U.S. Application Data

(60) Provisional application No. 62/573,864, filed on Oct. 18, 2017.

(51) Int. Cl.
    *H01J 35/32*     (2006.01)
    *G01V 5/12*     (2006.01)
    *G01N 23/203*     (2006.01)

(52) U.S. Cl.
    CPC ............ *H01J 35/02* (2013.01); *H01J 35/025* (2013.01); *H01J 35/32* (2013.01)

METHODS AND MEANS FOR CASING, PERFORATION AND SAND-SCREEN EVALUATION USING BACKSCATTERED X-RAY RADIATION IN A WELLBORE ENVIRONMENT

TECHNICAL FIELD

The present invention relates generally to methods and means for monitoring and determining casing and sand-screen integrity within wellbore environments.

BACKGROUND

Within the oil & gas industry, it is very important to accurately gauge the quality of casings. The industry currently employs various methods for the verification of the quality of the casing. Typically, calipers or cameras are employed to determine whether the casing/tubing is cylindrical and or not-corroded. However, cameras require the wellbore to contain optically clear fluids; otherwise, they are incapable of distinguishing features within the fluid/borehole. More recently, ultrasonic tools are run within the well in an attempt to image the casing/tubing, or elements outside of the tubing, such as the parts of a downhole safety valve. However, ultrasonic tools are model dependent, so prior knowledge of the precise makeup and status of the well is typically required for the ultrasound data to be compared against.

No viable technologies are currently available which use a method or means to employ a combination of collimators, located cylindrically around an X-ray source, located within a non-padded concentrically-located borehole logging tool, together with a single or plurality of rotatable two dimensional per-pixel collimated imaging detector array(s) to also be used as the primary imaging detector(s), to produce complete backscatter images of the casing/tubing.

Prior art teaches a variety of techniques that use x-rays or other radiant energy to inspect or obtain information about the structures within or surrounding the borehole of a water, oil or gas well, yet none teach a method or system to use first order detectors (which are typically used to compensate for mud-cake/fluid variations) to create a photograph-like image of the casing itself.

U.S. Pat. No. 7,675,029 to Teague et al. teaches an apparatus wherein the measurement of x-ray backscattered photons from any horizontal surface inside of a borehole admits to two-dimensional imaging techniques.

U.S. Pat. No. 8,481,919 to Teague teaches a method of producing Compton-spectrum radiation in a borehole without the use of radioactive isotopes. The reference further teaches rotating collimators around a fixed source installed internally to the apparatus but does not have solid-state detectors with collimators. It further teaches the use of conical and radially symmetrical anode arrangements to permit the production of panoramic x-ray radiation.

U.S. Pat. No. 7,705,294 to Teague teaches an apparatus that measures backscattered x-rays from the inner layers of a borehole in selected radial directions, with the missing segment data being populated through movement of the apparatus through the borehole. The apparatus permits generation of data for a two-dimensional reconstruction of the well or borehole, but the publication does not disclose the necessary geometry for the illuminating x-ray beam to permit discrimination of the depth from which the backscattered photons originated, rather, only the direction.

U.S. Pat. No. 3,564,251 to Youmans discloses the use of a azimuthally scanning collimated x-ray beam to produce an attenuated signal at a detector for the purposes of producing a spiral-formed log of the inside of a casing or borehole surface immediately surrounding the tool, effectively embodied as an x-ray caliper. However, the reference fails to teach or suggest a means or method to create a photo-like image, other than a two-dimensional radial plot on an oscilloscope.

U.S. Pat. No. 7,634,059 to Wraight discloses an apparatus that may be used to produce individual two-dimensional x-ray images of the inner surface inside of a borehole using a single pin-hole camera without the technical possibility to ascertain the azimuth of the image being taken, so that a tessellation/stitching of multiple images is also not disclosed.

US2013/0009049 by Smaardyk discloses an apparatus that allows measurement of backscattered x-rays from the inner layers of a borehole. However, the reference fails to disclose a means or method to create photo-like two dimensional images of the inner surfaces of the casing while the tool is being axially moved ('logged') through the wellbore so that a consolidated two-dimensional image of the well casing can be produced.

U.S. Pat. No. 8,138,471 to Shedlock discloses provides a scanning-beam apparatus based on an x-ray source, a rotatable x-ray beam collimator, and solid-state radiation detectors enabling the imaging of only the inner surfaces of borehole casings and pipelines. However, the reference fails to disclose a means or method to create photo-like two dimensional images of the inner surfaces of the casing while the tool is being axially moved ('logged') through the wellbore so that a consolidated two-dimensional image of the well casing can be produced.

U.S. Pat. No. 5,326,970 to Bayless discloses a tool that attempts to measure backscattered x-rays azimuthally in a single direction in order to measure formation density, with the x-ray source being based on a linear accelerator. However, the reference fails to teach a means or method to create photo-like two dimensional images of the inner surfaces of the casing while the tool is being axially moved ('logged') through the wellbore so that a consolidated two-dimensional image of the well casing can be produced. It also fails to teach or suggest a method and means that uses a fixed conical/panoramic beam to illuminate the well casing, whereas the directional collimation is located at the rotating detector.

U.S. Pat. No. 5,081,611 to Hornby discloses a method of back projection to determine acoustic physical parameters of the earth formation longitudinally along the borehole using a single ultrasonic transducer and a number of receivers, which are distributed along the primary axis of the tool.

U.S. Pat. No. 6,725,161 to Hillis discloses a method of placing a transmitter in a borehole and a receiver on the surface of the earth, or a receiver in a borehole and a transmitter on the surface of the earth, with the aim to determine structural information regarding the geological materials between the transmitter and receiver.

U.S. Pat. No. 6,876,721 to Siddiqui discloses a method to correlate information taken from a core-sample with information from a borehole density log. The core-sample information is derived from a CT scan of the core-sample, whereby the x-ray source and detectors are located on the outside of the sample, and thereby configured as an outside-looking-in arrangement. Various kinds of information from the CT scan such as its bulk density is compared to and correlated with the log information.

U.S. Pat. No. 4,464,569 to Flaum discloses a method to determine the elemental composition of earth formations surrounding a well borehole by processing the detected neutron capture gamma radiation emanating from the earth formation after neutron irradiation of the earth formation by a neutron spectroscopy logging tool.

U.S. Pat. No. 4,433,240 to Seeman discloses a borehole logging tool that detects natural radiation from the rock of the formation and logs said information so that it may be represented in an intensity versus depth plot format.

U.S. Pat. No. 3,976,879 to Turcotte discloses a borehole logging tool that detects and records the backscattered radiation from the formation surrounding the borehole by means of a pulsed electromagnetic energy or photon source, so that characteristic information may be represented in an intensity versus depth plot format.

U.S. Pat. No. 8,664,587 to Evans et al. discloses a method and means for creating azimuthal neutron porosity images in a logging while drilling environment. Since bottom hole assembly based systems historically relied upon the rotation of the drill string to assist in the acquisition of azimuthally dependent data, the reference discusses an arrangement of azimuthally static detectors which could be implemented in a modem BHA that does not necessarily rotate with the bit, by subdividing the neutron detectors into a plurality of azimuthally arranged detectors which are shielded within a moderator to infer directionality to incident neutrons and gamma.

U.S. Pat. No. 9,012,836 to Wilson et al. discloses a method and means for creating azimuthal neutron porosity images in a wireline environment. Similar to U.S. Pat. No. 8,664,587, the reference discusses an arrangement of azimuthally static detectors which could be implemented in a wireline tool to assist an operator in interpreting logs post-fracking by subdividing the neutron detectors into a plurality of azimuthally arranged detectors, which are in turn shielded within a moderator to infer directionality to incident neutrons and gamma.

U.S. Pat. No. 4,883,956 to Manente et al. discloses an apparatus and method for investigation of subsurface earth formations, in particular using an apparatus adapted for movement through a borehole. Depending upon the formation characteristic or characteristics to be measured, the apparatus may include a natural or artificial radiation source for irradiating the formations with penetrating radiation such as gamma rays, x-rays or neutrons. The light produced by a scintillator in response to detected radiation is used to generate a signal representative of at least one characteristic of the radiation and that signal is recorded.

U.S. Pat. No. 6,078,867 to Plumb discloses a method for generating a three-dimensional graphical representation of a borehole, comprising the steps of: receiving caliper data relating to the borehole, generating a three-dimensional wire mesh model of the borehole from the caliper data, and color mapping the three-dimensional wire mesh model from the caliper data based on either borehole form, rugosity and/or lithology.

SUMMARY

An x-ray-based cased wellbore environment imaging tool is provided, the tool including at least an x-ray source; a radiation shield to define the output form of the produced x-rays; a direction controllable two-dimensional per-pixel collimated imaging detector array; sonde-dependent electronics; and a plurality of tool logic electronics and PSUs.

A method of using an x-ray-based cased wellbore environment imaging tool to monitor and determine the integrity of materials within wellbore environments is also provided, the method including at least the steps of: producing x-rays in a shaped output; measuring the intensity of backscatter x-rays returning from materials surrounding the wellbore; controlling two-dimensional per-pixel collimated imaging detector arrays; and converting image data from said detectors into consolidated images of the wellbore materials.

BRIEF DESCRIPTION OF SEVERAL EXAMPLE EMBODIMENTS

The methods and means described herein for casing integrity evaluation while simultaneously imaging equipment/features located immediately surrounding the borehole, through x-ray backscatter imaging in a cased wellbore environment, is disclosed in a package so as to not require direct physical contact with the well casings (i.e., non-padded). The methods and means disclosed herein further comprise the use of a combination of collimators, located cylindrically around an X-ray source located within a non-padded concentrically-located borehole logging tool, together with a single or plurality of rotatable two dimensional per-pixel collimated imaging detector array(s) to also be used as the primary imaging detector(s). The ability to control the viewing direction of the collimated detectors permits the operator to either log the tool through the well casing while the detectors rotated azimuthally, to produce a two dimension helical ribbon backscatter x-ray image, or to hold the tool stationary as the collimated detector rotates azimuthally to capture a cylindrical image that can be improved upon 'statically' (as the detector continues to recapture casing images that can be added to the existing image set), and/or to actuate the detector such that a closer inspection of a particular region may be performed by pan-tilt control of the collimated detector.

In one example embodiment, an x-ray-based casing imaging tool [101] is deployed by wireline conveyance [103. 104] into a cased borehole [102], wherein the well casing or tubing [102] is imaged. The tool is enclosed by a pressure housing that ensures well fluids are maintained outside of the housing.

Figure 1:
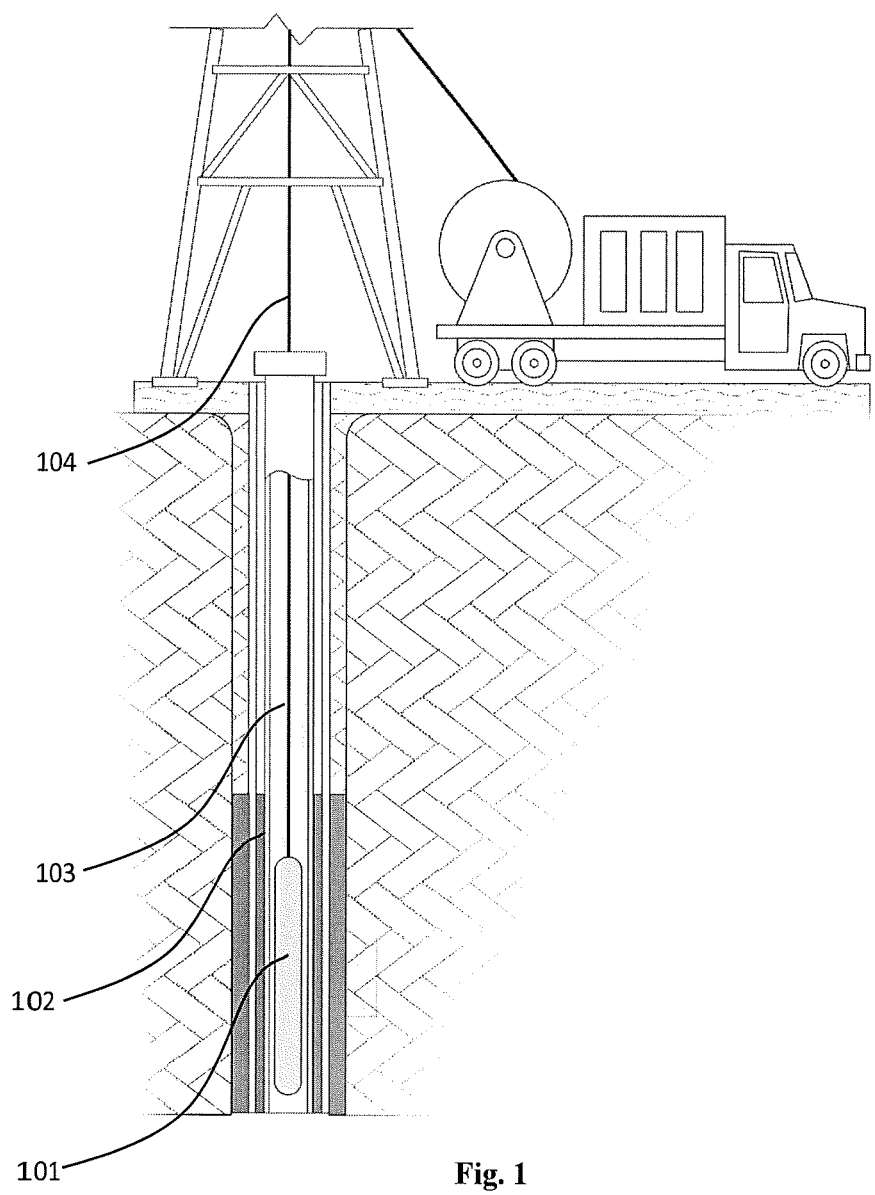
FIG. 1 illustrates an x-ray-based casing imaging tool being deployed into a borehole via wireline conveyance. Regions of interest within the materials surrounding the borehole are also indicated.
Figure 2:
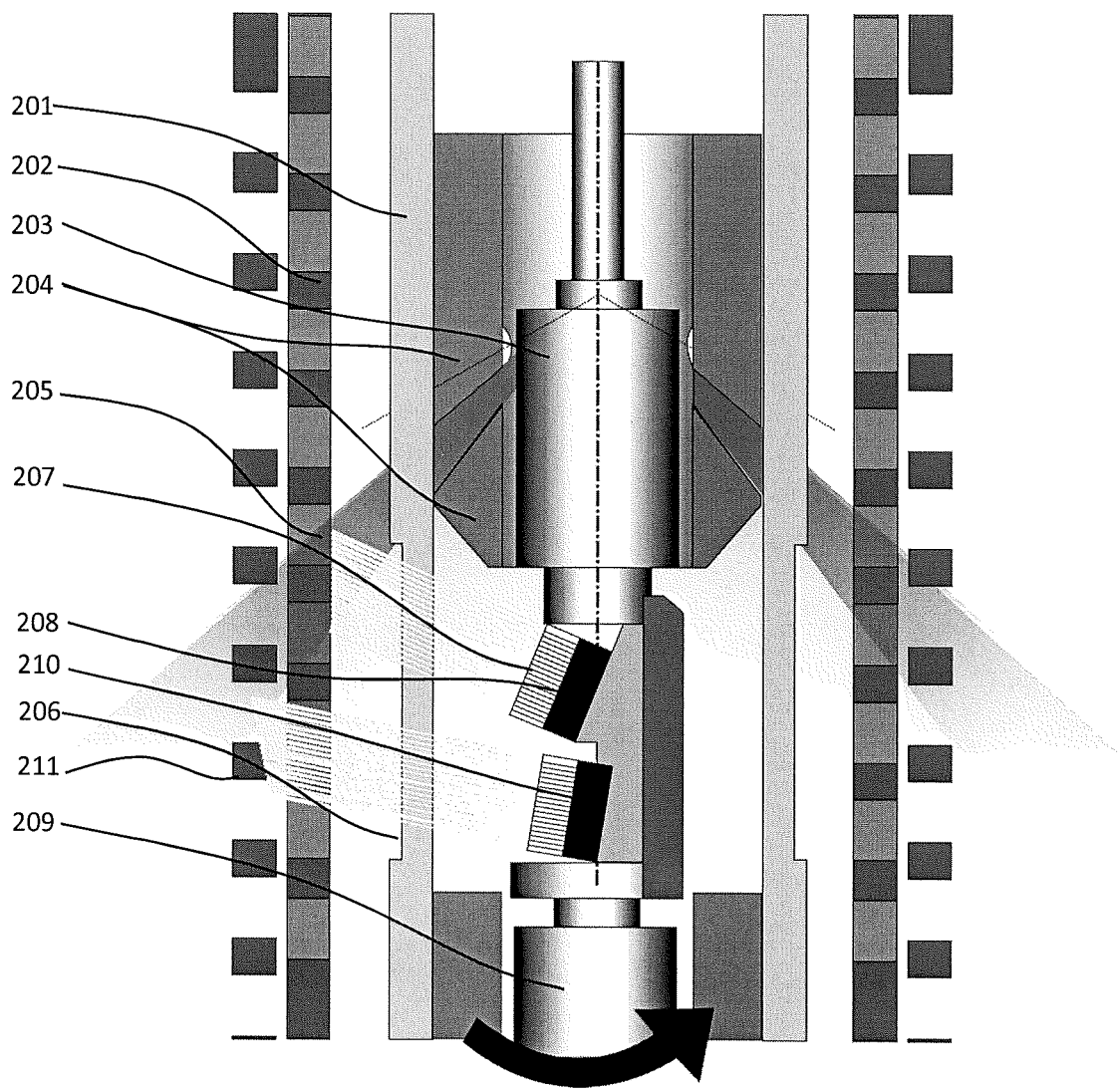
FIG. 2 illustrates one example of an x-ray-based casing imaging tool, arranged so as to enable imaging of the inner-most casing or tubing in addition to segments of the materials located outside of the casing or tubing.

FIG. 2 illustrates a pressure housing [201] that is conveyed through a well casing or tubing [202]. The pressure housing contains an electronic x-ray source [203] configured to produce x-rays panoramically in a conical output, the shape and distribution of said x-ray output is determined by the geometry of the collimator [204], which is formed by creating a non-blocking region of the radiation shielding. The conical x-ray beam illuminates a cylindrical section of the casing/tubing [205]. The radiation scattering from the casing is imaged by a two-dimensional detector array [208], which is attached to a per-pixel array collimator [207]. The detector collimator [207] reduces the field of view of each pixel of the detector array [208] such that each pixel images a distinct and unique section of the illuminated casing/tubing [205]. A motor/servo [209] is used to rotate the detector azimuthally, such that the collimated detector array images the illuminated ring section of the casing/tubing [205]. A further detector assembly [210] rotates upon the same armature but is geometrically configured to image a section of the wellbore that is illuminated by the x-rays but lays outside of the inner surfaces of the tubing/casing [211]. While the motor/servo [209] rotates the collimated detector arrays [207, 208, 210], back-scatter images are acquired by the detector of both the casing/tubing and the materials behind the casing/tubing. As the tool is being conveyed through the wellbore, the result is a helical ribbon of stacked images, with two distinct radial depths of investigation.

In a further example embodiment, the deeper depth of radial inspection detector assemblies are used to create images of sand-screens, to aid inspection.

In a further example embodiment, the deeper depth of radial inspection detector assemblies are used to create images of perforations, to aid inspection.

In a further embodiment still, the deeper depth of radial inspection detector assemblies would be used to create images of gravel-packs, to aid inspection.

In another embodiment, as the detector assembly rotates azimuthally, each axial 'column' of pixels of the detector arrays are sampled such that each column would image a similar section of the casing/tubing that had been imaged by its neighbor prior during the last sample. Upon encoding the images with the known azimuthal capture position of the image section, the separate image pixel columns associated with each imaged 'slit' section of the casing/tubing could be summated/averaged to produce a higher quality image within a single pass.

In yet another embodiment, two detectors are used back-to-back facing outwards, or side-by-side facing opposite directions, for each detector set, such that when the detector assembly is rotated, a double-helical image ribbon is produced as the tool is conveyed through the wellbore.

In another embodiment, 'n' detectors are used facing outwards, or arranged for maximal volumetric packing efficiency, for each detector assembly position, such that when the detector assembly is rotated, n-helical image ribbons are produced for each radial depth being images, as the tool is conveyed through the wellbore.

In another embodiment, the logging speed and detector assembly rotational rate are matched such, that a single azimuthal rotation of the detector assembly is performed while the tool is conveyed axially by one imaged axial tubing/casing section [9] height, such that the resulting images of the casing/tubing, and the outer layer 'skin' is complete and helically welded.

In a further embodiment, the detector assemblies' rotation and axial/radial tilt are controlled through the use of servos/actuators such that the operator may stop the tool within the borehole and inspect certain sections of the casing/tubing (i.e. without the detector assembly being in continual rotation mode).

In a further embodiment, the operator can stop the conveyance of the tool and use the azimuthal rotation of the detector assembly to continually sample the same images tubing/casing illuminated cylinder [9] section, such that the resulting data set can build/summate statistically to improve image quality.

In another embodiment, the backscatter images also comprise spectral information so that a photo-electric or characteristic-energy measurement may be taken, and the imaged material analyzed for scale-build up, casing corrosion, etc.

In a further embodiment, machine learning is employed to automatically analyze the spectral (photo electric or characteristic energy) content of the images to identify key features, such as corrosion, holes, cracks, scratches, and/or scale-buildup.

In a further embodiment, the per-pixel collimated imaging detector array further comprises a single 'strip' array (i.e., one pixel wide azimuthally) and multiple pixels long axially—the imaging result is then a 'cylindrical' ribbon image. When the tool is moved axially (either by wireline-winch or with a stroker, for example) and a new image set taken, a section of casing is imaged by stacking cylindrical ribbon images/logs.

In a further embodiment, machine learning is employed to automatically reformat (or re-tesselate) the resulting images, as a function of depth and varying logging speeds or logging steps, such that the finalized casing and/or cement image is accurately correlated for azimuthal direction and axial depth, by comparing with CCL, wireline run-in measurements, and/or other pressure/depth data.

The foregoing specification is provided only for illustrative purposes, and is not intended to describe all possible aspects of the present invention. While the invention has herein been shown and described in detail with respect to several exemplary embodiments, those of ordinary skill in the art will appreciate that minor changes to the description, and various other modifications, omissions and additions may also be made without departing from the spirit or scope thereof.

The invention claimed is:

1. A method of using an x-ray-based cased wellbore environment imaging tool to monitor and determine the integrity of materials within wellbore environments, said method comprising:
    producing x-rays in a panoramically conical output;
    measuring the intensity of backscatter x-rays returning from associated casing, perforated casing or sand screen enveloping the wellbore fluid;
    using a controller to control an azimuthal orientation of at least two two-dimensional per-pixel collimated imaging detector arrays; and
    converting image data from said detectors into consolidated images of the wellbore materials.

2. The method of claim 1, further comprising using said imaging detector to create two-dimensional per-pixel collimated imaging detector arrays wherein the imaging array is one pixel wide and multiple pixels long.

3. The method of claim 1, further comprising using said imaging detectors to create a plurality of more than two two-dimensional per-pixel collimated imaging detector arrays.

4. The method of claim 1, further comprising matching a rotation rate of the imaging detectors to an axial logging speed of said tool in order to create a continuous helical image ribbon without blind regions.

5. The method of claim 1, further comprising continuously rotating the imaging detectors while said tool is stationary within the wellbore in order to produce statistically accumulated cylindrical images over the same region of the wellbore.

6. The method of claim 1, further comprising using spectral information to inform the characteristics of any wellbore materials or debris.

7. The method of claim 1, further comprising forming said shield from tungsten.

8. The method of claim 1, further comprising using the tool to determine the position, distribution and area of perforations within the casings surrounding the cased wellbore.

9. The method of claim 1, further comprising using the tool to determine the position and integrity of sand-screens within the casings surrounding the cased wellbore.

10. The method of claim 1, further comprising using machine learning to automatically reformat or re-tesselate the resulting images as a function of depth and varying logging speeds or logging steps.

* * * * *